US00PP08852P

United States Patent [19]

Gruppe et al.

[11] Patent Number: Plant 8,852

[45] Date of Patent: Aug. 2, 1994

[54] CHERRY ROOTSTOCK GI 148/8

[75] Inventors: Werner Gruppe, Linden; Hanna Schmidt, Ahrensburg, both of Fed. Rep. of Germany

[73] Assignee: Inter-Plant Patent Marketing, Inc., Niagara-on-the-Lake, Canada

[21] Appl. No.: 921,171

[22] Filed: Jul. 29, 1992

[51] Int. Cl.[5] ..... A01H 5/00

[52] U.S. Cl. ..... Plt./37

[58] Field of Search ..... Plt. 37

[56] References Cited

PUBLICATIONS

Perry, R. L., "Cherry Rootstocks" *Rootstocks for Fruit Crops* (Rom, et al., Eds.) John Wiley & Sons, N.Y. 1987, pp. 251–254.

Registration documents for 173/9 and 148/2.

German publication "Giessen 1991" Red Book.

German publication "Giessen 1991" Green Book.

Newspaper clipping dated Sturday, Feb. 15, 1992.

Cherry Rootstock NC–140, 1990.

Miscellaneous German Test Data.

*Primary Examiner*—James R. Feyrer

*Attorney, Agent, or Firm*—Dykema Gossett PLLC

[57] ABSTRACT

The new and distinct cultivar of cherry rootstock, which has been given the designation GI 148/8 produces a tree which is generally spreading and which upon grafting produces a dwarf tree.

3 Drawing Sheets

FIELD OF THE INVENTION

The present invention relates generally to cherry trees and more specifically to a new and distinct variety of cherry hybrid tree which is particularly useful as a rootstock.

BACKGROUND OF THE INVENTION

The new and distinct variety of cherry hybrid tree of the present invention was bred by the inventors as a cross of *Prunus cerasus* cv. "Schattenmorelle" with *Prunus canescens* in Giessen, Germany. It has been successfully asexually propagated by softwood cuttings at the University of Giessen in Giessen, Germany, and has been observed to remain true to the description set forth herein. In one test planting in Kassel, Germany, 148/8 was chip-budded with a mean success of 72%.

SUMMARY OF THE INVENTION

The new and distinct cultivar of cherry rootstock, which has been given the designation GI 148/8 produces a tree which is generally spreading and which upon grafting produces a dwarf tree.

DETAILED DESCRIPTION OF THE INVENTION

Figure 1:
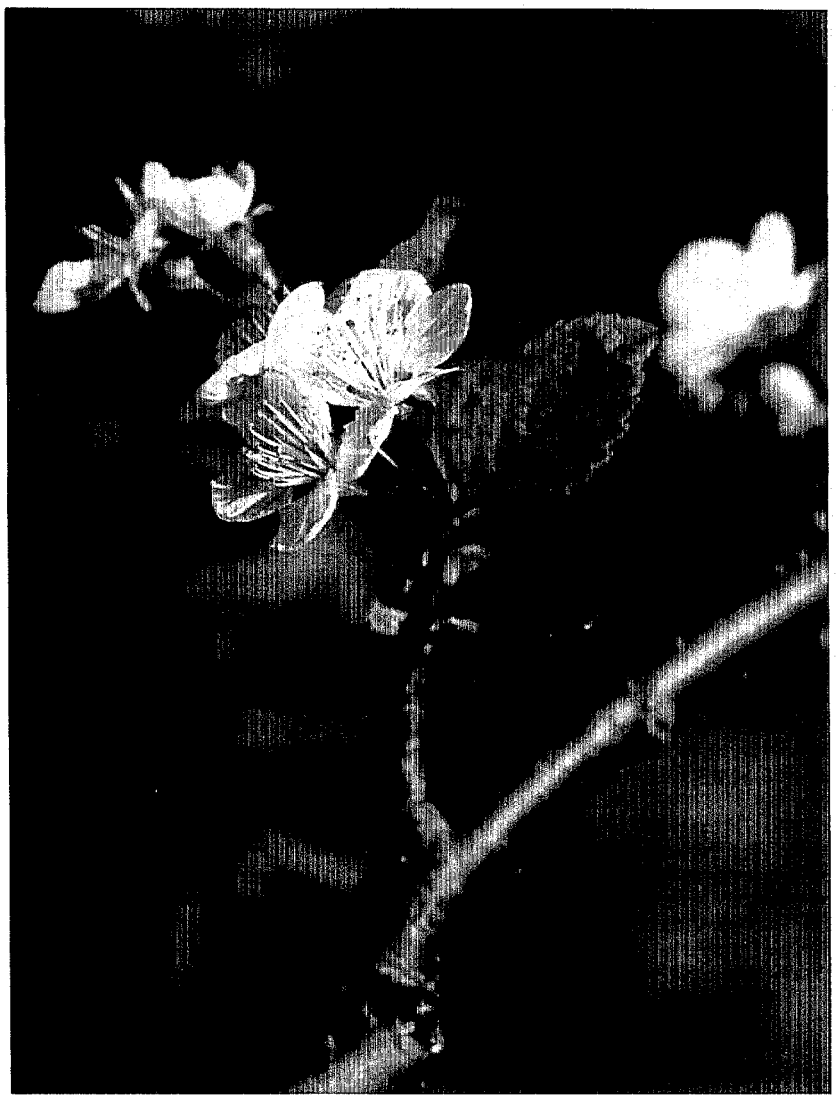
FIG. 1 illustrates a branch and bloom of GI 148/8.
Figure 2:
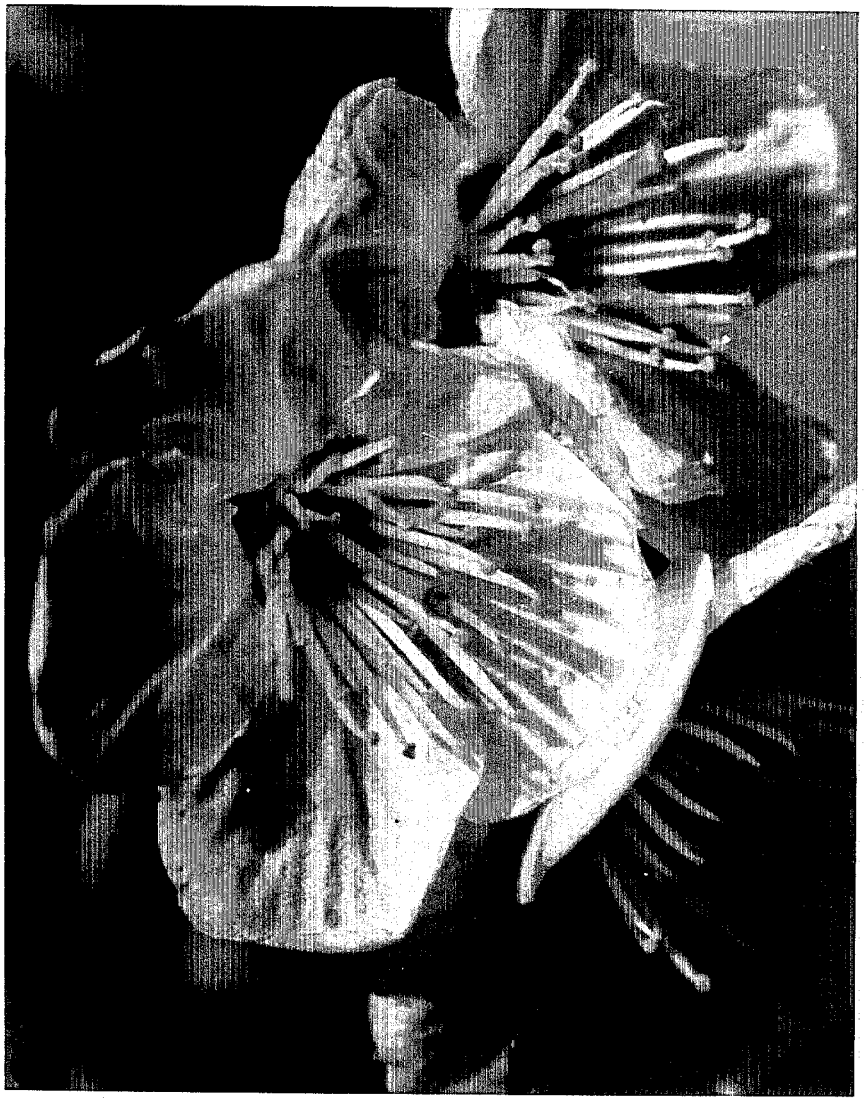
FIG. 2 illustrates GI 148/8 flowers.
Figure 3:
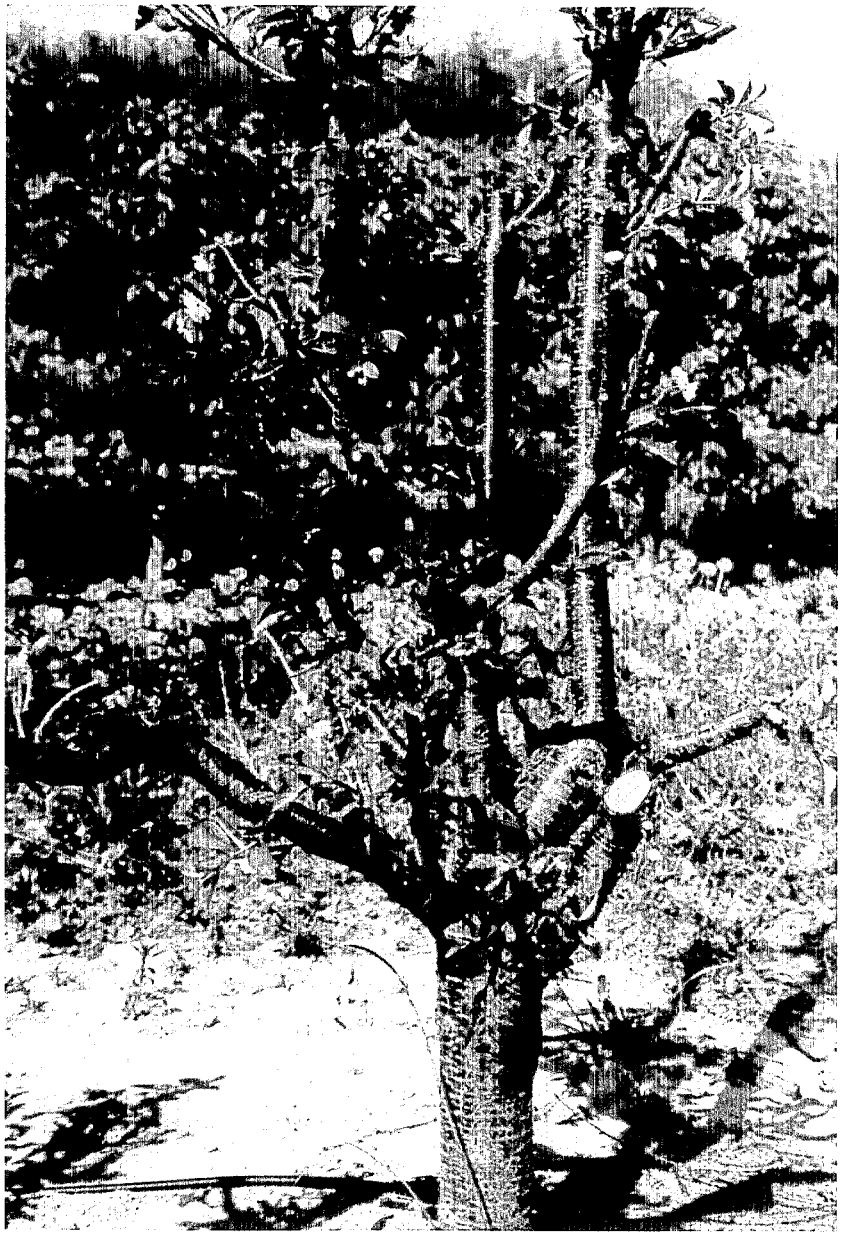
FIG. 3 is a whole tree view of 148/8.

GI 148/8 as used as a rootstock for sweet cherry trees induces dwarfing to a significant degree. In comparison with rootstock F12/1, GI 148/8 produces 30 percent of growth, as measured as the fresh weight of the upper tree parts of cv. "Hedelfinger" after 12 years in orchards near Giessen, Germany. Precosity, high production of fruit and yield efficiency, good 100-fruit weight and no or very few suckers were induced. GI 148/8 as a rootstock confers earlier and heavier bearing to the scion as compared to F12/1 clonal cherry rootstock. In one trial, it induced a yield in the variety "Hedelfinger" in the 5th leaf of 4.9 kg/tree (cf. F12/1: 0.2 kg/tree) and in the 7th leaf of 18.8 kg/tree (cf. F12/1: 5.7 kg/tree). As a mean of seven years, 100-fruit-weight of "Hedelfinger" grafted on 148/8 was 754 grams, while 100-fruit-weight of "Hedelfinger" grafted on F12/1 was 735 grams.

GI 148/8 itself is semi-drooping. After eight growing seasons near Giessen, Germany, GI 148/8 demonstrated a height of 1.30 meters and a width of 2.20 meters. GI 148/8 is sensitive to the virus PNRV, tolerant to the virus PDV, and medium sensitive to "Pfeffinger disease." It has a sufficient tolerance to water-logging.

The following varieties of sweet and sour cherries have been successfully grafted onto GI 148/8: Hedelfinger Riesenkirsche, Büttners Rote Knorpel, Grosse Schwarze Knorpel, Van, Gold, Ulster, Bing, Early Burlat, Emperor Francis, Querfurter Königskirsche, Napoleon, Rainier, Sam, Schmidt, Schneiders Späte Knorpel, Stella, Vega, Vic, Viva, Windsor, Hudson, Lambert; Montmorency, Meteor, Rubinweichsel, Morellenfeuer, North Star, Schattenmorelle, Rheinische Schattenmorelle, Ludwigs Frühe, Leitzkauer, Nabella, Successa, Schwäbische Weinweichsel. No graft incompatibility is presently known.

Ploidy of 148/8 is probably triploid ($2n=3\times$). The ploidy status of the parents has been investigated by isoemzyme analysis and is tetraploid ($2n=4\times$) for the mother plant=*Prunus cerasus*, "Schattenmorelle", and diploid ($2n=2\times$) for the father plant, *Prunus canescens*.

Leaves:

*Overall shape.*—Oval.

*Length-to width ratio.*—2.0.

*Apex shape.*—Acuminated.

*Base shape.*—Acuminated.

*Leaf serration.*—Doubly serrate.

*Pubescence.*—Pubescent.

*Color.*—Light green.

Leaf dimensions:

*Mean length of leaves.*—7.6 cm (F12/1: 10/7 cm).

*Mean width of leaves.*—3.8 cm (F12/1: 5.3 cm).

*Mean length of petioles.*—1.4 cm (F12/1: 2.6 cm).

Branches:

*Thickness of one year branch.*—2.2 mm diameters.

*Color.*—Redbrown-grey.

*Overall.*—1-year old branches are sparsely pubescent, lenticels on 1-year old branches are light cream colored, 0.5 mm diameter, buds alternate, with 2–5 buds at base of 1st years growth, 19 nodes on 1-year old branches. Branch and lenticel color are not considered to be distinguishing characteristics.

Branch dimensions: (For a single GI 148/8 plant in the ungrafted condition after the 5th leaf; in brackets, comparable data for F12/1).

*Mean length of 1-year-old branches.*—21.2 cm (19.8 cm).

*Mean length of 2-year-old branches.*—18.2 cm (35.0 cm).

*Mean length of 3-year-old branches.*—36.6 cm (63.2 cm).

*Mean diameter of 1-year-old branches.*—2.2 mm (3.4 mm).

*Mean diameter of 2-year-old branches.*—4.0 mm (5.8 mm).

*Mean diameter of 3-year-old branches.*—6.6 mm (10.1 mm).

*Mean no. of branches from 2-year-old branches.*—1.4 (0.7).

*Mean no. of branches from 3-year-old branches.*—2.0 (2.4).

Mean no. of nodes of *2-year-old branches.*—11.4 (15.3).

*Mean no. of nodes of 3-year-old branches.*—17.0 (22.4).

Mean angle of *3-year old branches.*—68.9 (59.7).

*Mean angle of 4-year old branches.*—74.0 (58.3).

Buds: Conical, acute, adpressed, 2–3 mm long, overlapping bud scales, with prominent leaf scars. No ornamental value.

Flowers:

*Flowering.*—Very late flowering.

*Abundance.*—Medium.

*Petal color.*—White.

*Petal shape.*—Reniform with rounded tip.

*Petal length/width ratio.*—2.2:3.0.

*Filaments.*—Coarse, generally erect.

Bloom:

1973.—Begin of bloom at May 7th.

1984 and 1985.—At the 2nd of May not yet popcorn stage.

1987.—May 6th just passed popcorn stage.

Overall vigor:

*Ungrafted.*—Very weak.

*Suckers.*—No suckers in unworked condition; few suckers grafted with "Hedelfinger".

Root system: Exceptional total length of roots and a high percentage of very thin roots; 93–94 percent of the roots are thinner than 5 mm diameter.

Survey of growth data: Growth of clones, not grafted, 60 kilometers south of Giessen, Germany.

*Planted.*—Autumn 1972; cut down to the ground Spring 1981.

*Measurements.*—After 8 years (fresh weight): height 1.3 meters, width 2.2 meters, depth 2.7 meters, fresh weight 3.0 kg.

*General.*—Very weak growing, broad.Growth of clones grafted with "Hedelfinger Riesenkirsche" 60 kilometers south of Giessen, Germany.

*Planted.*—Nov. 1975.

*Rooted out.*—Apr. 1988 (after 12 years in orchard) mean values of three trees with F12/1 standard (also mean value of three trees).

| | GI 148/8 | F12/1 |
|---|---|---|
| Height of Crown (Winter 87/88) | 2.9 m | 5.2 m |
| Width of Crown (Winter 87/88) | 4.1 m | 6.2 m |
| Stem Cross Sectional Area of Variety (Winter 87/88) | 259 $cm^2$ | 503 $cm^2$ |
| Stem Cross Sectional Area of Rootstock (Winter 87/88) | 117 $cm^2$ | 486 $cm^2$ |
| Fresh Weight of Plant Parts Above Ground (April 88) | 53.5 kg | 176 kg |
| Weight in Percent | 30.4% | 100% |

Crown-silhouette (m2)=height × (width+depth)/2:

| | 148/8 | F12/1 |
|---|---|---|
| at the end of 1979 = after 4 years in orchard: | 6.6 | 7.7 |
| at the end of 1980 = after 5 years in orchard: | 8.2 | 11.5 |
| at the end of 1981 = after 6 years in orchard: | 10.1 | 14.3 |

Enzyme polymorphism: (Studied by horizontal starch gel electrophoresis of leaf tissue of 8 loci.). The results for 148/8 and 148/1 are:

| | 148/1 | 148/8 |
|---|---|---|
| Aconitase-2 | 24 | 2 |
| Alkoholdehydrogenase-1 | 112 | 1 |
| Isocitratdehydrogenase-2 | 112 | 112 |
| Leucinaminopeptisase-1 | 34 | 34 |
| 5-Phosphogluconat-Dehydrogenase-1 | 112 | 112 |
| 6-Phosphogluconat-Dehydrogenase-2 | 122 | 122 |
| Phophoglucose-Isomerase-2 | 224 | 224 |
| Phosphoglucomutase-2 | 25 | 25 |

General comparative data: In order to further distinguish 148/8 from its siblings, 148/1 and 148/9, the following comparative data are set forth for the latter two varieties:

148/1.—Provides 67 percent of growth, and measures at the height of the upper parts of "Hedelfinger" as compared to rootstock F12/1 after 12 years in orchards near Giessen, Germany. GI 148/1 is generally erect and medium strong in growth. Ungrafted, 148/1 exhibits medium strong vigor.

148/9.—Is sensitive to PNRV. Does require support and has few suckers; yield of "Hedelfinger" on 148/1 typically much greater than on 148/9 and vigor of "Hedelfinger" less on 148/9 than 148/1.

What is claimed is:

1. A new and distinct variety of cherry hybrid tree as shown and described herein.

* * * * *

UNITED STATES PATENT AND TRADEMARK OFFICE

CERTIFICATE OF CORRECTION

PATENT NO. : Plant 8,852
DATED : August 2, 1994
INVENTOR(S) : Gruppe et al.

It is certified that error appears in the above-indentified patent and that said Letters Patent is hereby corrected as shown below:

Column 2, line 14, the word "Grosse" should be --Grobe--

Signed and Sealed this

Twenty-ninth Day of November, 1994

*Attest:*

Bruce Lehman

BRUCE LEHMAN

*Attesting Officer*

*Commissioner of Patents and Trademarks*